(12) United States Patent
Lattner (10) Patent No.: US 10,925,803 B2
(45) Date of Patent: Feb. 23, 2021

(54) METHOD AND APPARATUS FOR TREATING VARIOUS NEUROLOGICAL CONDITIONS

(76) Inventor: Stefanie Lattner, Viera, FL (US)

(*) Notice: Subject to any disclaimer, the term of this patent is extended or adjusted under 35 U.S.C. 154(b) by 1180 days.

(21) Appl. No.: 13/978,298

(22) PCT Filed: Jan. 5, 2012

(86) PCT No.: PCT/US2012/020315
§ 371 (c)(1),
(2), (4) Date: Jul. 3, 2013

(87) PCT Pub. No.: WO2012/094484
PCT Pub. Date: Jul. 12, 2012

(65) Prior Publication Data
US 2013/0303953 A1     Nov. 14, 2013

Related U.S. Application Data

(60) Provisional application No. 61/430,040, filed on Jan. 5, 2011.

(51) Int. Cl.
*A61H 23/00*     (2006.01)
*A61M 21/00*     (2006.01)
(Continued)

(52) U.S. Cl.
CPC ......... *A61H 23/00* (2013.01); *A61H 23/0245* (2013.01); *A61M 21/00* (2013.01); *A61H 2201/1604* (2013.01); *A61H 2201/165* (2013.01); *A61H 2201/5002* (2013.01); *A61H 2201/5097* (2013.01); *A61H 2205/027* (2013.01); *A61H 2230/065* (2013.01); *A61H 2230/305* (2013.01); *A61H 2230/405* (2013.01); *A61H 2230/505* (2013.01); *A61M 21/02* (2013.01); *A61M 2021/0022* (2013.01);
(Continued)

(58) Field of Classification Search
CPC ... A61H 23/00; A61H 23/0245; A61M 21/00; A61M 21/02; A61N 1/0456; A61N 1/0541
See application file for complete search history.

(56) References Cited

U.S. PATENT DOCUMENTS 4,667,676 A * 5/1987 Guinta ................. A61B 5/4863
128/908
5,241,967 A * 9/1993 Yasushi .............. A61B 5/04842
600/27
(Continued)

FOREIGN PATENT DOCUMENTS

WO    2008143371 A1    11/2008
WO    2010043413 A1    4/2010

OTHER PUBLICATIONS

Supplementary European Search Report for corresponding European Patent Application No. 12732164.4 dated May 28, 2014.
(Continued)

*Primary Examiner* — LaToya M Louis
(74) *Attorney, Agent, or Firm* — Slavitt IP Law (57) ABSTRACT

Methods and apparatus for treating neurological conditions such as attention deficit disorder, autism, and Parkinson's disease. More particularly, methods and apparatus used to stimulate the 8th cranial nerve, particularly for treatment of such diseases and disorders.

17 Claims, 9 Drawing Sheets

(51) Int. Cl.
*A61H 23/02* (2006.01)
*A61M 21/02* (2006.01)

(52) U.S. Cl.
CPC .............. *A61M 2021/0027* (2013.01); *A61M 2021/0072* (2013.01); *A61M 2205/50* (2013.01); *H04R 2460/13* (2013.01)

(56) References Cited

U.S. PATENT DOCUMENTS

| | | | |
|---|---|---|---|
| 6,430,443 B1 * | 8/2002 | Karell | A61N 1/36032 607/55 |
| 7,613,519 B2 * | 11/2009 | De Ridder | A61N 1/0529 607/55 |
| 2002/0072781 A1 | 6/2002 | Lattner | |
| 2003/0195588 A1 * | 10/2003 | Fischell | A61N 2/02 607/55 |
| 2005/0267549 A1 * | 12/2005 | Della Santina | A61N 1/36032 607/57 |
| 2006/0205994 A1 | 9/2006 | Sunnen | |
| 2007/0239227 A1 * | 10/2007 | Fridman | A61N 1/36032 607/57 |
| 2008/0081941 A1 | 4/2008 | Tononi | |
| 2009/0082831 A1 | 3/2009 | Paul et al. | |

OTHER PUBLICATIONS

Office Action Communication for corresponding European Patent Application No. 12732164.4 dated Aug. 25, 2016.

* cited by examiner

Minimally Invasive:

METHOD AND APPARATUS FOR TREATING VARIOUS NEUROLOGICAL CONDITIONS

CROSS-REFERENCE TO RELATED APPLICATIONS

This application claim priority to U.S. provisional patent application No. 61/430,040 filed on Jan. 5, 2011 in the name of Stefanie Lattner entitled "Method and Apparatus for Treating Various Neurological Conditions", which is hereby incorporated by reference in its entirety.

FIELD

The present invention relates to a method and apparatus for treating neurological conditions such as attention deficit disorder, autism, and Parkinson's disease. More particularly, the invention relates to methods and apparatus used to stimulate the $8^{th}$ cranial nerve, particularly for treatment of such diseases and disorders.

BACKGROUND

Figure 1A:
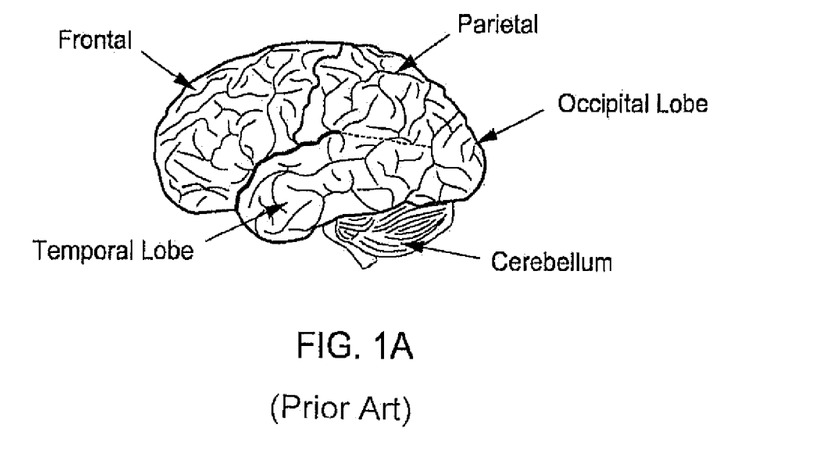
FIG. 1A is a depiction of the human brain, showing various parts, including the vestibulocochlear nerve (i.e. the $8^{th}$ cranial nerve).
Figure 1B:
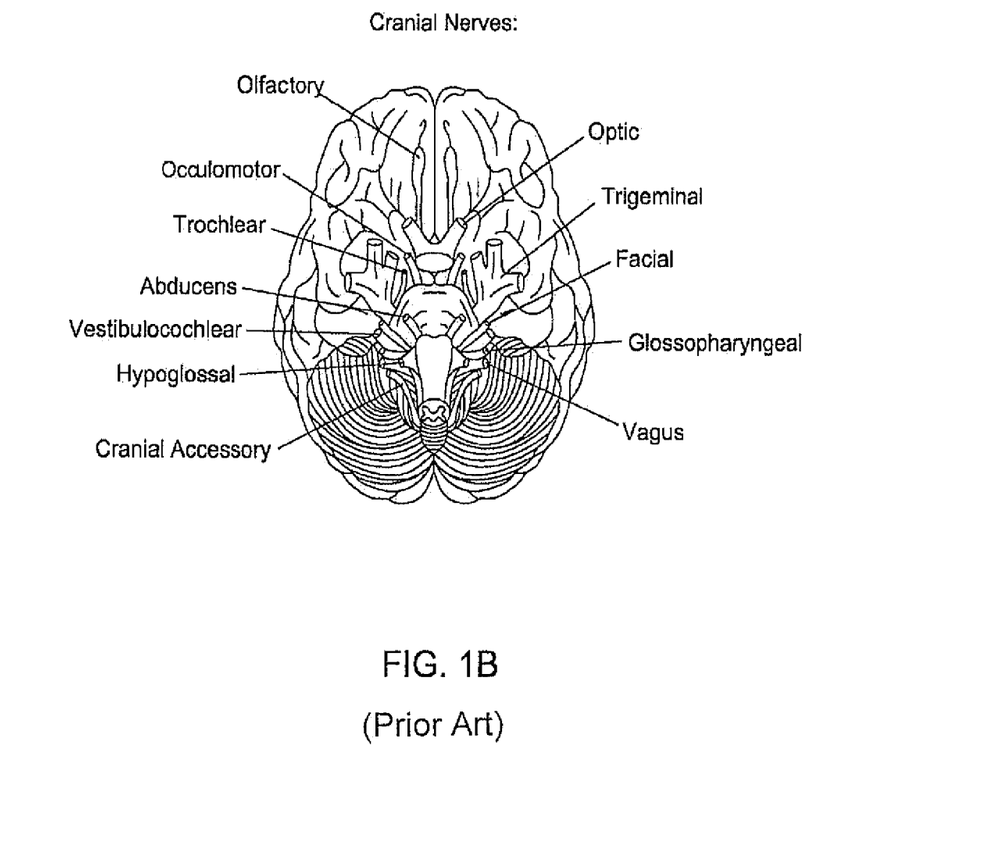
FIG. 1B depicts the human brain, showing the various portions or lobes of the brain.

The $8^{th}$ cranial nerve is comprised of the auditory nerve and the vestibular nerve which are adjacent to each other. Fibers of the vestibular nerve are excited (fire) at different frequencies than the auditory nerve. See FIG. 1 for a diagram of the brain and the location of the $8^{th}$ cranial nerve.

Previous devices have been focused on specific designs that uniquely stimulate either the auditory nerve or the vestibular nerve for the purpose of hearing or balance respectively and without interfering with the other. For example, vestibular stimulators were designed to stimulate the vestibular bundle while not creating any auditory affects (i.e. create the sensation of rocking without the device causing any noise, pinging, buzzing, or other unwanted auditory excitation); while cochlear implants are designed to stimulate the auditory nerve without effecting the vestibular nerve (excite the nerve fibers of the auditory bundle without causing vertigo).

Previous vestibular stimulation devices were designed to cause an end-effect that results in sleepiness and even sleep. Thus, such devices were specifically designed to be worn during sleep, and need not concern themselves with wake-time activities such as vision and coordination of movement while awake. Other such devices were designed to induce the sensation of rocking.

Previous devices for stimulation of either the auditory nerve or the vestibular nerve accomplished stimulation through electrical transduction. Prior devices employed the use of electrodes as the primary mechanism to influence the targeted nerve. These devices deliver electrical energy in or near the head for the purpose of stimulating nerves. Such electrical devices inherently contain safety risks as electrical energy is delivered directly to brain tissue and can be difficult to contain as it (by definition) will change the electrical potential of all cells within a certain distance and time of administration. If the electrical energy is not adequately contained or if it is delivered at the wrong amplitude or frequency, tissue damage may result.

These devices simply were not capable of or designed to treat the disorders contemplated herein. Accordingly, there is a need for a method and device capable of stimulating both the vestibular and the auditory nerves, particularly for treatment of neurological disorders such as attention deficit disorder, autism, and Parkinson's disease.

SUMMARY

Some embodiments provide a method for treating a neurological disorder, the method comprising applying at least one stimulus to the vestibulocochlear nerve of a patient in need of such treatment, wherein the at least one stimulus is an auditory stimulus, a vibratory stimulus, or a combination thereof. In some instances, both auditory stimulus and vibratory stimulus are applied. In some instances, the at least one stimulus is applied to one of the vestibulocochlear nerves in others, it may be applied to both vestibulocochlear nerves.

In some embodiments, the auditory stimulus is applied at a frequency of about 0.1 Hz to about 40 Hz.

In some embodiments, the vibratory stimulus is applied at a frequency of about 0.3 Hz to about 15 Hz.

In some embodiments, an auditory stimulus is applied to each vestibulocochlear nerve at different frequencies.

In some embodiments, an auditory stimulus is applied to an auditory nerve bundle of the vestibulocochlear nerve, without affecting a vestibular nerve bundle.

In some embodiments, a vibratory stimulus is applied to a vestibular nerve bundle, without affecting an auditory nerve bundle.

In some embodiments, the at least one stimulus is applied externally and travels to the vestibulocochlear nerve via transmission through body tissues In some embodiments, the at least one stimulus is applied within the patient's body and transmitted either directly to the vestibulocochlear nerve or via transmission through body tissues.

Some embodiments provide a method of increasing concentration, the method comprising applying at least one stimulus to the vestibulocochlear nerve of a patient in need of such treatment, wherein the at least one stimulus is an auditory stimulus, a vibratory stimulus, or a combination thereof, and causes an increase in Beta brain wave activity.

Some embodiments provide a method of enhancing relaxation, the method comprising applying at least one stimulus to the vestibulocochlear nerve of a patient in need of such treatment, wherein the at least one stimulus is an auditory stimulus, a vibratory stimulus, or a combination thereof, and causes an increase in alpha brain wave activity.

Some embodiments provide an apparatus for delivering a stimulus to the vestibulocochlear nerve of a patient, the apparatus comprising at least one vibratory element adapted capable of delivering auditory stimulus between 0.1 Hz and about 40 Hz, vibratory stimulus between about 0.3 Hz and about 15 Hz, or both; and a microprocessor, operatively coupled to the vibratory element for controlling the delivery of stimuli via the at least one vibratory element.

Some embodiments further comprise a second vibratory element adapted capable of delivering auditory stimulus between 0.1 Hz and about 40 Hz, vibratory stimulus between about 0.3 Hz and about 15 Hz, or both, wherein the at least one vibratory element and the second vibratory element are independently controllable by the microprocessor.

DETAILED DESCRIPTION OF THE INVENTION

It is believed that through optimal stimulation of the entire vestibularcochlear nerve (not just the vestibular bundle or auditory bundle) the devices described herein can be used to treat a variety of neurological disorders, such as, but not limited to attention deficit disorder, autism, and Parkinson's disease. Fibers of the vestibular nerve fire at different frequencies than the auditory nerve, so the stimulator incorporates techniques that optimally trigger and sustain the correct stimulation of both sets of nerve fibers which requires sophisticated coupling and sensitivity to the desired vs. undesired end effects.

Some embodiments of the invention are designed to cause an end-effect that, rather than inducing sleepiness, increases concentration (which may be an excitatory effect in the brain—particularly when targeted at treating ADHD). Similarly with autism, stimulation may increase neuronal development, interconnections and/or improve synchrony, all of which are believed to be lacking in patients suffering from autism.

Some embodiments of the invention are based on mechanical vibration, and is consequently safer than previous devices and methods employing electrical transmissions. The mechanical vibration will not change the electrical potential of all cells within the area and will only affect those cells capable of mechanical transduction.

This invention is designed to stimulate the $8^{th}$ cranial nerve, the vestibulochoclear nerve, for the purpose of treating dibilitating effects of ADD, autism, parkinsons, etc. . . . including anxiety, lack of concentration, lack of motor control, and hyperactivity.

As described above, the vestibulocochlear nerve is a sensory nerve that comprises the auditory branch and the vestibular branch. It transduces external information into neuronal signals that the brain then integrates, processes, and reacts to. As is well known, the nerve branches that comprise the vestibulocochlear nerve are predominantly responsible for hearing and balance. However, the neural pathways of this sensory neuron further connect to the thalamus and cortex through complex interactions that are under investigation, but not fully understood. It is suspected that these sensory inputs may have the ability to influence memory, emotion, concentration, etc. Anatomically there exists evidence that the portions of the vestibulocochlear nerve connects with areas of the brain indicated in each of the disorders mentioned including the temporal lobe, frontal lobe, and the cerebellum through the thalamus in in the case of the vestibular projections, directly to the cerebellum. The vestibular projections are also known to communicate with the extraoccular motor nuclei, comprising the vestibulo-occular reflex which stabilizes vision and balance. This neural reflex also directly communicates with the cerebellum for motor control. The exact neural interactions per each disorder of interest, however, is not yet known.

Key neurotransmitters that are under investigation with respect to these disorders, namely, but not exclusively, dopamine and seratonin are also indicated in early animal studies as being modulators of the vestibulocochlear nerve. While the neurobiology of this invention is not well understood due to the early nature of the scientific community's understanding of the neurobiology of the brain, it is believed that stimulating this nerves through artificial means such as the device described herein, influences the key neurotransmitters in a way that results in the desired clinical end-effect.

Figure 2:
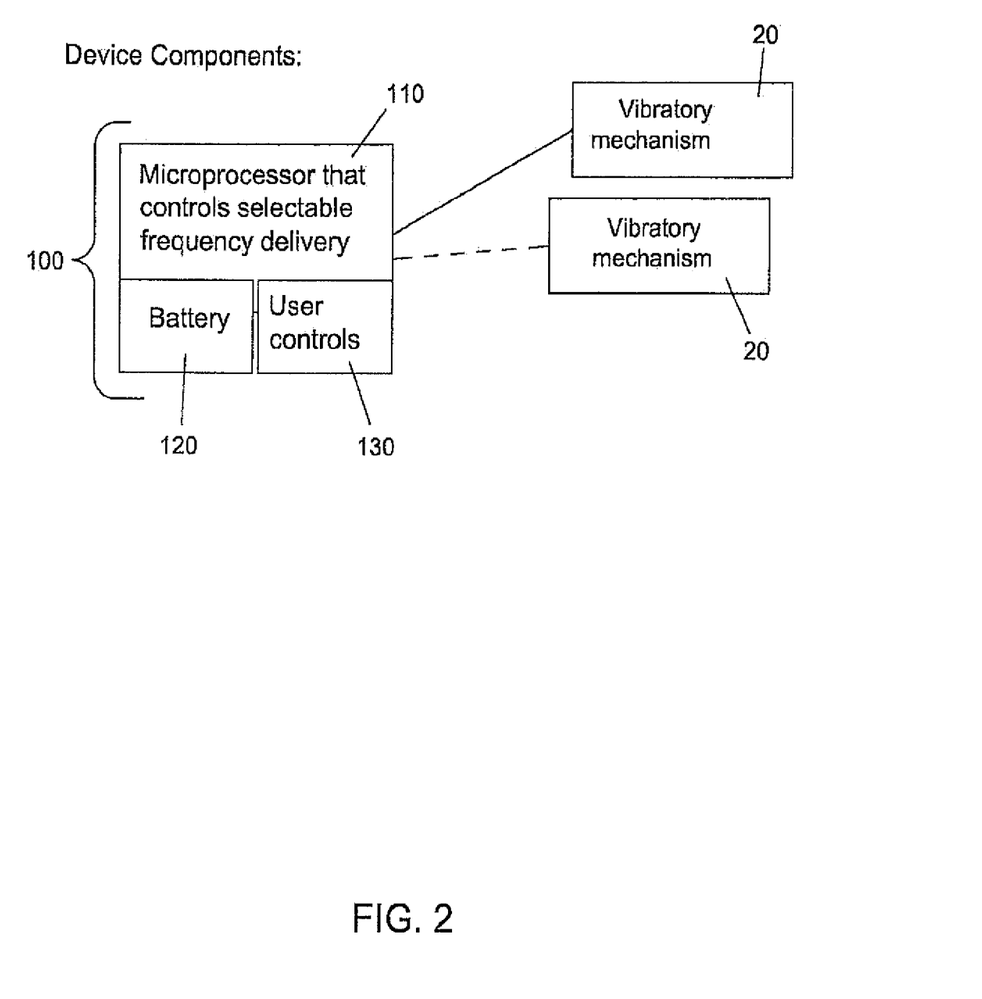
FIG. 2 is a schematic drawing of a device according to some embodiments.

FIG. 2 shows a basic schematic of a device 10 in accordance with one embodiment of the invention.

Unlike prior devices for stimulating the vestibucochlear nerve:

The device is not intended to stimulate the auditory branch of this nerve for the purpose of effecting hearing.

The device is not intended to stimulate the vestibular branch of this nerve for the purpose of effecting balance or to create a sensation of rocking.

Both of these nerve branches optimally fire at different frequencies (discussed in the device description below). The device is designed to optimally stimulate the $8^{th}$ cranial nerve (both branches) while not stimulating any neighboring nerves (such as the facial nerve).

The auditory bundle is integrated in the brain using contralateral control (opposite side), while the vestibular portion of the nerve is controlled on the ipsilateral side (same side). The delivery of stimulus and the reaction to that stimulus is complex. The invention described herewith comprised techniques to address this complexity by optimizing each type of stimulus needed and optimally combining them if and when needed.

The device 10 employs a vibrating mechanism 20 to mechanically stimulate the nerves, a control module 100, which can include a microprocessor 110, optional user controls 120, and a power source, such as a battery 130. The vibrating mechanism 20 can be any suitable mechanism known or later developed in the art. Some exemplary vibrating mechanisms include but are not limited to "coin" or "pancake" vibration motors, ceramic devices, piezo actuators, puffers (for air or liquid), etc.

In some embodiments, the device is an electromechanical device that comprises an embedded microprocessor/controller that causes contacts to vibrate at a predetermined force and frequency to stimulate the $8^{th}$ cranial nerve as described herein. The device can be designed to be completely non-invasive device, a minimally invasive device, or fully implantable device.

The device delivers a complex vibration (comprised of specifically selected frequencies) that is capable of optimally stimulating each bundle of the nerve, without stimulating neighboring nerves.

The device stimulates the nerve without delivering electrical energy (greatly improving the safety profile of the device).

The device is designed so that when built in the non-invasive form, is capable of securing to the back of the ear at the junction of the cranial bone and mandible.

The device comprises a microprocessor for controlling the selection of frequencies to be delivered, as well as the delivery thereof, as well as one or more vibratory mechanisms, and in some embodiments at least 2 vibratory mechanisms. The vibratory mechanism(s) are operatively coupled to the microprocessor which may be powered by a battery or other power source. The device may also be provided with a user interface and controls for powering the device on or off, and other controls.

The device can be constructed in a number of ways and may employ various existing or later developed vibrator mechanisms.

In some non-invasive embodiments, the following options may be employed. Particularly, the vibratory mechanism can be located in the ear canal, and/or behind the ear at the junction of cranium and jaw line. The mechanism of vibration can be achieved by creating changes in air pressure, applying a mechanical force, pulsation of fluid (encapsulated water, air, saline, etc), or a combination of the above. To secure the mechanism behind the ear any suitable material may be used, including but not limited to a gel pillow (or any soft material that transfers the vibration at the desired frequency), a spring-loaded actuator, a skin-friendly sticky pad, or any combination of the above. Some devices are adapted for insertion into the ear canal, these include but are not limited to a bladder filled with air, gel, saline, soft silicone, or similar with vibrating element embedded, a probe fitted to the ear canal that channels pulsating air, saline, or similar (as a mechanism for transducing the selected frequency). In some embodiment a combination of both in the ear canal and externally applied vibratory mechanisms can be employed.

The device can either be controlled automatically via the microprocessor or allow for user control of any of a variety of options. For example the microprocessor/controller may be Time-based: For example, on for X minutes with an intentional off-period to control therapy time. In other embodiments, it can be User-controlled where the user has the option to turn on the device on an as-needed basis (with limits programmed to prevent any potential over-usage). The control may be staged, cycling the user through various stages in order to obtain the desired end effect. For example, you might start with one frequency mix for a specified duration and then adapt either over a fixed time, by user control, by algorithmic adaptation or adaptation based on physiological input/monitoring.

In some embodiments, the user's physiological condition or response can be used to control the device. Any physiological condition or combination thereof could be used to control the device or to determine how to control the device, including but not limited to heart rate, blood pressure, pulse, temperature, respiration, neurotransmitters such as serotonin, blood-based biomarkers, ear-fluid-based biomarkers, selectable therapy/frequencies for specific conditions. Delivery of therapy/frequencies via a programmed algorithm that controls spatial and temporal separation so that the brain can adequately interpret and react to the stimulus may also be used. There is also a diagnostic option for titration or for separate application.

Stimulus Options:

The auditory and vibratory stimuli applied can be administered independently or combined, depending on the specific treatment approach. Specific frequencies can be tailored to each nerve bundle and then combined, if desired.

Suitable Preferred frequencies ranges include:

Vestibular Bundle: 0.1 Hz-15 Hz

Auditory bundle: 0.3 Hz-40 Hz (through any of the methods listed below)

Carrier frequency: 20 Hz-20 KHz (audible range)

Carrier frequency with specified frequencies for vestibular and auditory bundle combined.

Methods to administer stimulus to auditory stimulus:

Administer the desired frequency in one ear only.

Administer 2 stimuli to each ear such that the difference is the desired stimulus.

Frequency modulation (in terms of phase-modulation and optimizing harmonics) or in terms of the specific frequency chosen.

Force of vibration of air/fluid component (which could be considered amplitude modulation).

Preferred range: 0-90 dB

Force of vibration to skin-connecting elements: any range considered tolerable for wearing for longer durations.

Combination of any of the above.

Preferred embodiment:

Vestibular Stimulus delivered behind the ear with both vibrating elements tuned to 0.2-0.4 Hz. Plus Auditory stimulus also delivered behind the ear through a secondary vibratory element tuned such that one element vibrates at 80 Hz on one ear and the second at 40 Hz on the other ear. (So that all are below what is typically considered the auditory range).

Note: This represents only one example and is not meant to limit the potential options listed within.

Figure 3:
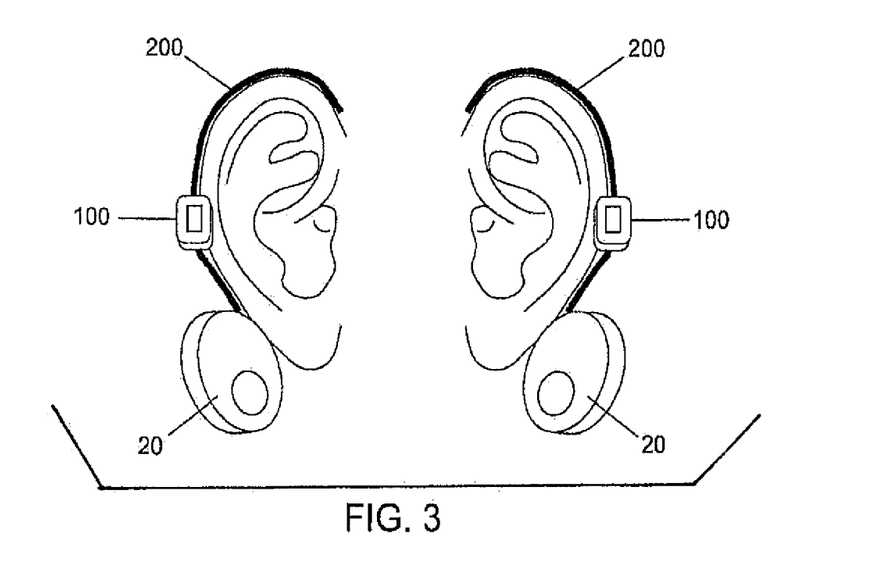
FIG. 3 is a graphical representation of a device according to some embodiments.

Depending upon the chosen features, particularly whether behind the ear or in the ear or both, the device can be constructed in a number of ways. For example, as seen in FIG. 3, a spring-loaded articulating arm 200 that positions the pad containing the vibrating mechanism 20 correctly and maintains contact with the skin with the correct amount of pressure can be employed. The microprocessor/controller 100 and battery can be directly connected to pad with the actuator on microprocessor/controller 100.

Figure 4:
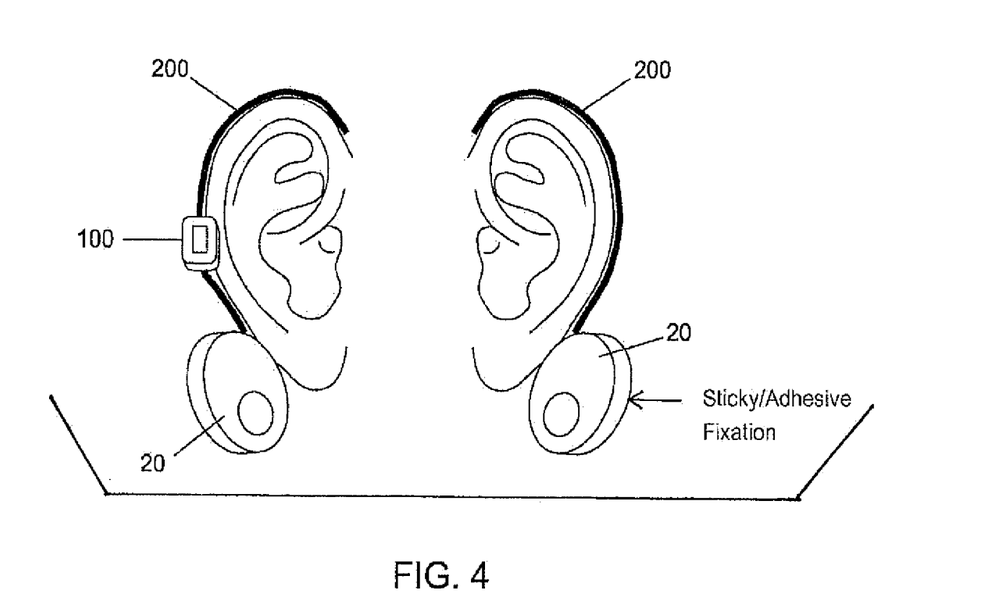
FIG. 4 is a graphical representation of an alternative device according to some embodiments.

In some embodiments, the device is adapted for use with both ears. In others, the device may be employed for one ear only (either ear) as shown in FIG. 4.

In some embodiments, an adhesive/sticky fixation may be used rather than spring-loading. Other suitable fasteners will be known to those of skill in the art.

Figure 5A:
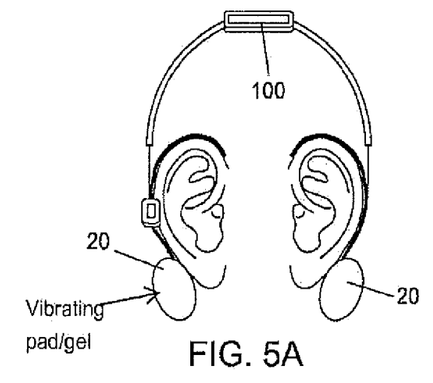
FIG. 5A is a graphical representation of an alternative device according to some embodiments employing a headset type arrangement and external vibrating elements.
Figure 5B:
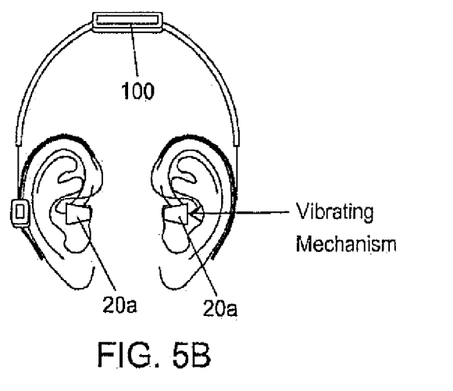
FIG. 5B is a graphical representation of an alternative device according to some embodiments employing a headset type arrangement and ear bud type vibrating elements.

In some embodiments, the microprocessor/controller and actuator are located on headset (shown with multiple fixating mechanisms), as seen in FIG. 5. FIG. 5 also depicts an embodiment employing the vibrating mechanism as an ear bud 20a, or other ear-canal device.

Figure 6A:
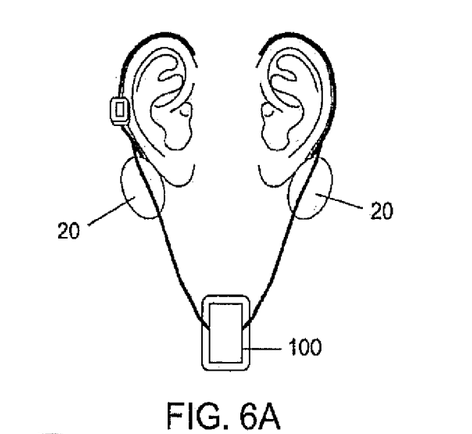
FIG. 6A is a graphical representation of an alternative device according to some embodiments employing a wearable device arrangement and external vibrating elements.
Figure 6B:
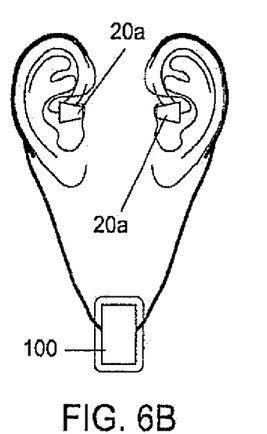
FIG. 6B is a graphical representation of an alternative device according to some embodiments employing a wearable device arrangement and ear bud type vibrating elements.

In some embodiments, the microprocessor/controller and actuator are located on wearable, connecting device (shown with multiple fixation methods), as seen in FIG. 6.

Figure 7A:
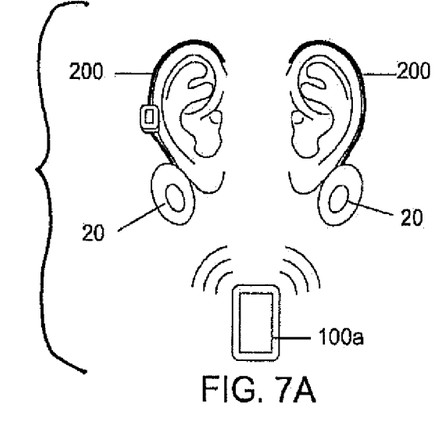
FIG. 7A is a graphical representation of an alternative device according to some embodiments employing a remote transmitter and external vibrating elements.
Figure 7B:
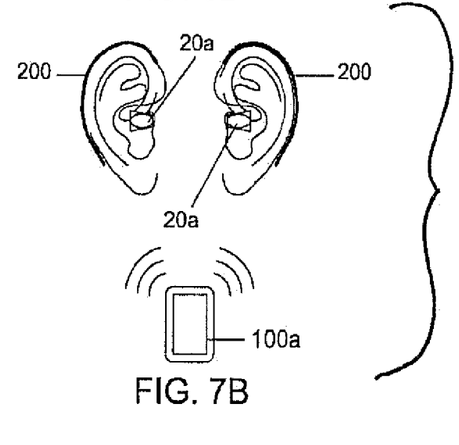
FIG. 7B is a graphical representation of an alternative device according to some embodiments employing a remote transmitter and ear bud type vibrating elements.

In some embodiments, the microprocessor/controller and actuator are located on a remote transmitting device (shown with multiple fixation methods), as seen in FIG. 7.

Figure 8A:
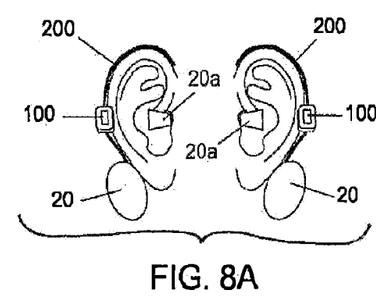
FIGS. 8A and 8B show two arrangement both employing both external vibrating elements and ear bud type vibrating elements.
Figure 8B:
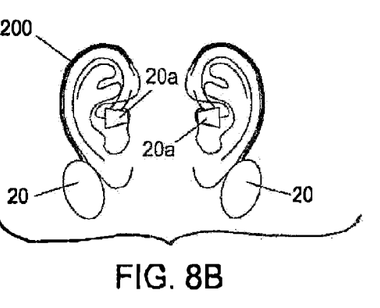

A dual vibrating mechanism may be employed is some embodiments above. FIG. 8 shows an exemplary embodiment.

Figure 9:
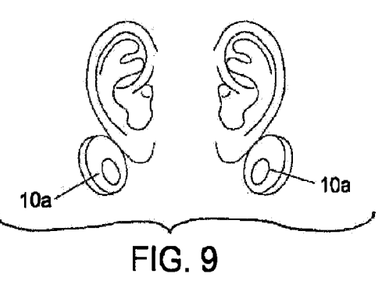
FIGS. 9 and 10 show a self-contained device in accordance with some embodiments, affixed either externally to the back of the ear, or within the ear canal.
Figure 10:
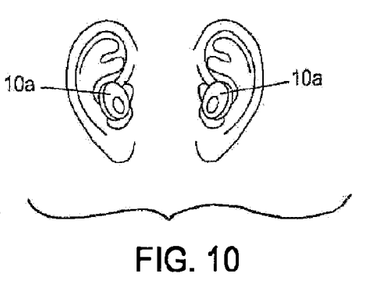

In some embodiments, exemplified in FIGS. 9 and 10, the device 10a is completely self-contained and fixed to the back of the ear or within ear canal.

Figure 11:
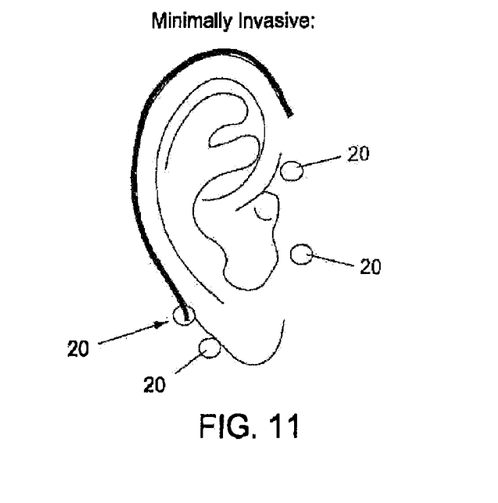
FIG. 11 shows a minimally invasive device, including potential attachment sites.

In some embodiments, the device is a minimally invasive, as shown in FIG. 11, employing a small injection for placement of vibrating element under the skin. The microprocessor/controller and actuator can be mounted externally as described above or in any suitable manner.

If transmitter is not used, the vibrating element may be connected via external skin contact.

Figure 12:
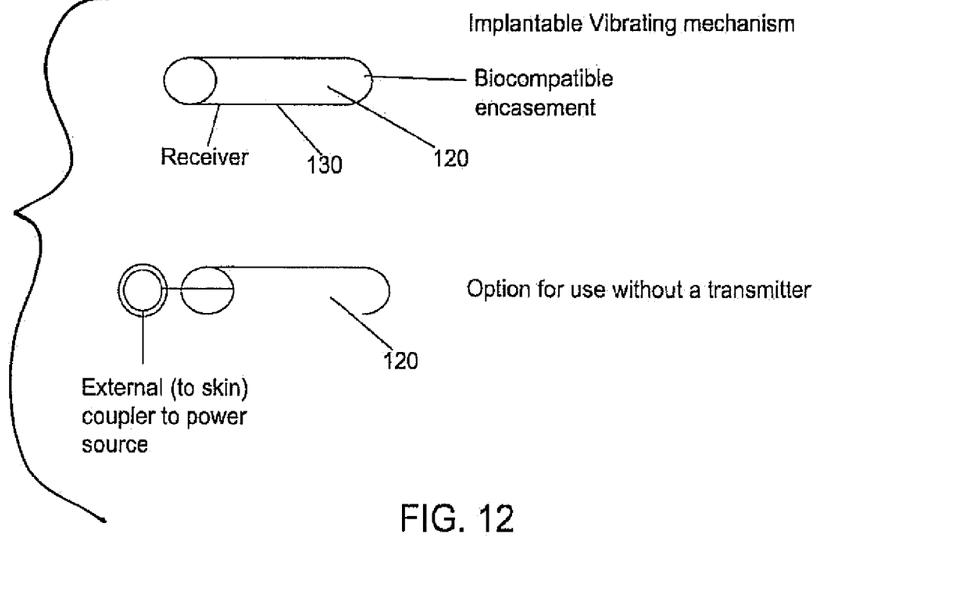
FIG. 12 depicts a schematic of an implantable device according to some embodiments.
Figure 13:
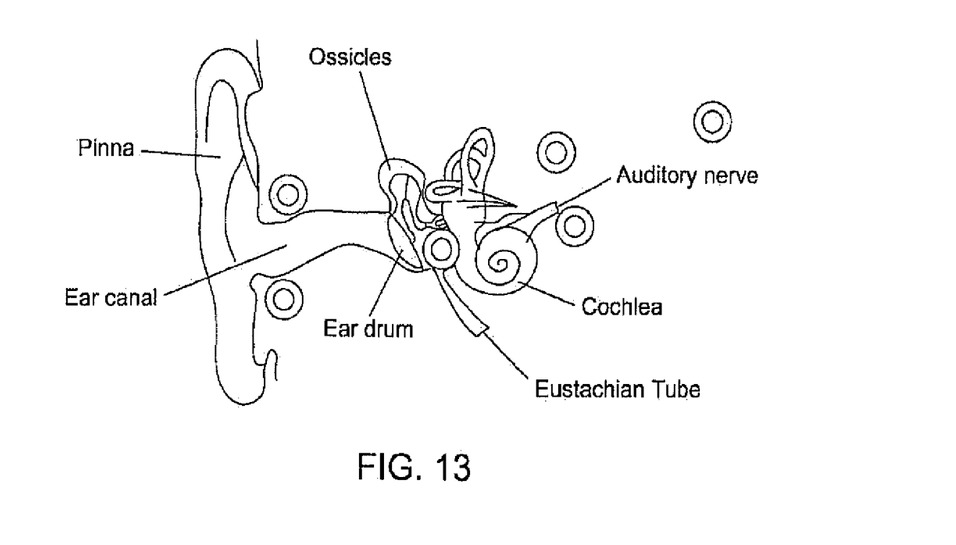
FIG. 13 depicts possible implantation sites.

In some embodiments, the device is implantable as shown in FIG. 12. In these embodiments, the device is located completely, or substantially completely, under the skin. Locations for the vibrating element 20 are similar to those described above for the minimally invasive device, but in these embodiments, the microprocessor/controller could also be implanted. The circles in FIG. 13 show exemplary locations for the vibrating element. Location of microprocessor/controller could be in soft tissue space and hard-wired to the vibrating element.

Also contemplated herein are methods of treating neurological disorders via mechanically stimulating the 8$^{th}$ cranial nerve in a patient in need of such treatment. In some embodiments, the neurological disorder to be treated is selected from ADHD, autism, and Parkinson's.

EXPERIMENTAL

An experimental test procedure was set up to determine and establish the effectiveness of the device to increase concentration or increase relaxation. To determine effectiveness, a standard EEG was used to measure various brain waves. The importance and interpretation of these was determined consistent with what is reported in the literature. Generally, increased alpha wave activity when the test subject's eyes are closed indicates increased relaxation. Increased Beta wave activity typically means the brain is awake and thinking (in general) and it does not necessarily mean excitation as might be interpreted from some graphs. In the prefrontal and sometimes frontal lobes, where interpretation and logic are performed, increased Beta wave activity suggests increased concentration. These channels are important to review when making assessments during math or reading tasks. As used herein, the various brain waves are:

Scoring Frequencies

Beta: >12.0 Hz
Alpha: 8-12 Hz
Theta: 4-7.5 Hz
Delta: 0.5-3.5 Hz
Set-Up and Test Method:
Test subject was an adult female with no known disorders related to ADD, ADHD, anxiety or any other condition. This clinical profile was chosen since it would represent the most difficult situation to improve upon with regard to increasing concentration or attention, or to improve relaxation.

Test subject was instrumented with a traditional "10-20" EEG lead placement on the scalp. Commercial neurophysiology software was used to acquire EEG data in real time during studies conducted during evening hours.

Studies were conducted to collect data across 19 leads with a sample rate of 1000 Hz, filtering for 60 Hz noise rejection (related to the common frequency used in the United States). Each study was initiated after each lead was calibrated and verified by the software to have minimal impedance (indicating a good connection to the scalp for signal acquisition).

Test Protocol:

The test protocol mimicked study protocols used for qEEG to study subjects with ADD, ADHD, Anxiety or other neurological disorders. This included the following sequence:

1. Sit relaxed with eyes open for up to several minutes (allowing subject to blink naturally)
2. Sit relaxed eyes closed for up to several minutes
3. Sit relaxed with eyes open for several minutes (allowing subject to blink naturally)
4. Complete Math Task for several minutes. This included counting backwards from a random number at an interval given at the beginning of the study (for example, start at X and count backwards by Y).
5. Complete Read Task for several minutes. This included reading several chapters of a book (the book presented was one that test subject had not seen/read prior)
6. Repeat the above protocol while wearing device with it turned on. Similar tasks with new starting material were undertaken. When the device is on, it has both vibration and an auditory element. In this case, the auditory element was the stimulation sound created by the vibrationmotor. The vibration stimulation consisted of a pressure element applied to the back of the ear. The vibration of the pressure sensor was generated using a sign wave with an amplitude of 2V peak-to-peak and a frequency of 0.5 hertz. The amplitude of the pressure sensor can be changed to ensure that the vibration is felt through the skin. The stimulus was applied for the full duration of this study protocol.).

Device Parameters:
Round in shape—12 mm (0.5") diameter, 3.4 mm (0.134") thick.
No visible moving parts.
Adhesive used on one side to fix to body
Placement: Behind ear, bilateral
Vibration Design:
2V, changeable peak-to-peak voltage amplitude,
0.5 Hz frequency (also changeable), bilateral
Waveform: Sine waveCapable of up to 1G vibration at 12,000 rpm from 3V with current less than 80 mA.
Auditory Design
Audible Frequency range used, bilateral
Analysis:

All data were recorded and annotated to mark events (task start, task stop, eye blinks, coughs, noticeable head movements, etc). As is customary in the field, representative sections were digitally analyzed and compared with and without using the device. FFT (fast Fourier transform) was the method used by software to present the spectral distribution. All results screens were generated automatically by the software. The tables were created using specific channel data reported by the software. No custom/home developed software was used to review or analyze the data.

Concentration

The subject was instrumented with the EEG electrodes and paced through a series of math and reading tasks while not wearing the device (control) and while wearing the device. The electrodes on the prefrontal cortex (FP1 and FP2) are key channels indicating concentration.

Figure 14:
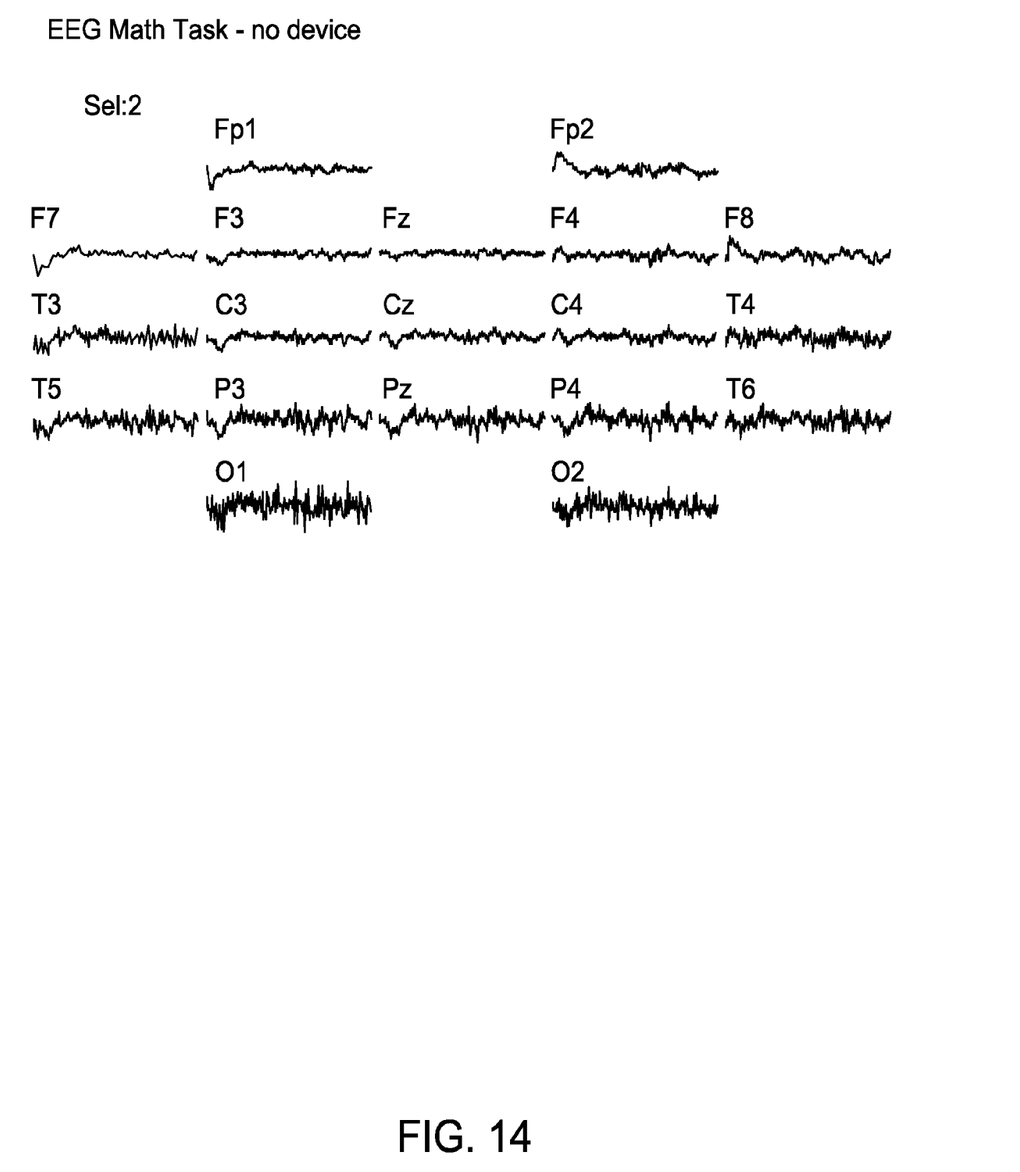
FIGS. 14-17 are EEG readouts under various testing conditions.

Math Task:

The table below shows a baseline reading of the test subject performing a math task without the device. The EEG readout is shown in FIG. 14, and generally indicates concentration during the math task.

Math Task - No Device
Predominance of the cerebral rhythms by channel

|  | Theta | Beta 1 | Beta 2 | Beta 3 | Theta/ (sum of Beta) |
|---|---|---|---|---|---|
| FP1 | 20.81% | 10.84% | 5.93% | 5.79% | 92.24% |
| FP2 | 16.24% | 11.47% | 7.76% | 6.23% | 63.79% |
| F7 | 19.60% | 13.51% | 8.06% | 6.76% | 69.18% |
| F8 | 17.07% | 16.11% | 8.68% | 7.54% | 52.80% |
| F3 | 18.76% | 16.97% | 10.62% | 7.76% | 53.07% |
| F4 | 19.87% | 19.58% | 8.47% | 8.12% | 54.94% |
| FZ | 20.06% | 14.78% | 7.11% | 8.20% | 66.67% |

FP1 & FP2 (Prefrontal cortex) are key channels indicating concentration Control

Figure 15:
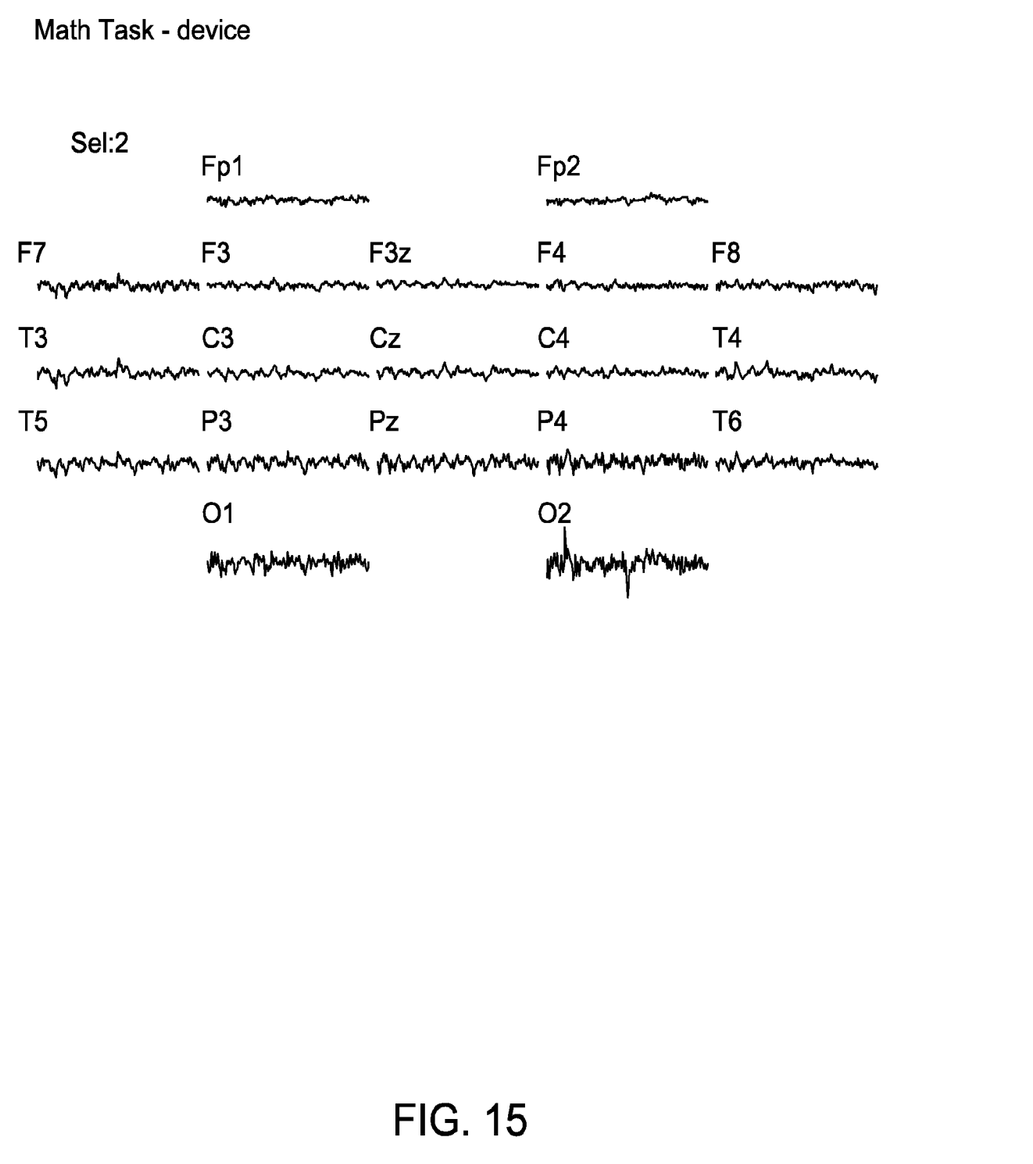

By comparison, the table below shows the same subject performing a similar math task while wearing the device. The results generally show increased Beta activity, and a decreased ratio of theta activity to beta activity. Each of these is generally indicative of an increase in concentration. The EEG readout is shown in FIG. 15 and supports the conclusion of increased concentration.

Mask Task - Device On
Predominance of the cerebral rhythms by channel

|  | Theta | Beta 1 | Beta 2 | Beta 3 | Theta/(sum of Beta) | Results* |
|---|---|---|---|---|---|---|
| FP1 | 16.28% | 19.27% | 18.28% | 17.98% | 29.32% | Decreased Theta/Beta |
| FP2 | 19.33% | 15.39% | 15.11% | 12.26% | 45.21% | Decreased Theta/Beta |
| F7 | 17.53% | 16.21% | 16.56% | 14.07% | 37.43% | Decreased Theta/Beta |
| F8 | 22.74% | 19.22% | 15.82% | 10.44% | 50.00% | Decreased Theta/Beta |
| F3 | 18.39% | 18.71% | 16.33% | 12.25% | 38.89% | Decreased Theta/Beta |
| F4 | 23.03% | 17.00% | 14.80% | 14.32% | 49.93% | Decreased Theta/Beta |
| FZ | 22.02% | 15.09% | 17.92% | 12.89% | 47.97% | Decreased Theta/Beta |

FP1 & FP2 (Prefrontal Cortex) are key channels indicating concentration
*Desired result is Decreased Theta/Beta indicating higher concentration The data above, indicate that the test subject appears to have a higher level of concentration while wearing the device.

Reading Task:

The table below shows a baseline reading of the test subject performing a reading task without the device.

Reading Task - No Device
Predominance of the cerebral rhythms by channel

|  | Theta | Beta 1 | Beta 2 | Beta 3 | Theta/(sum of Beta) |
|---|---|---|---|---|---|
| FP1 | 22.06% | 13.01% | 6.61% | 5.16% | 89.02% |
| FP2 | 22.44% | 13.77% | 6.46% | 5.12% | 88.52% |
| F7 | 19.22% | 15.72% | 8.43% | 7.23% | 61.25% |
| F3 | 22.06% | 15.45% | 9.76% | 6.81% | 68.89% |
| F8 | 23.23% | 15.76% | 8.44% | 5.50% | 78.22% |
| F4 | 21.28% | 17.34% | 10.25% | 6.08% | 63.20% |
| FZ | 23.93% | 14.66% | 8.59% | 6.21% | 81.23% |

FP1 & FP2 (Prefrontal Cortex) are key channels indicating concentration Control

By comparison, the table below shows the same subject performing a similar reading task while wearing the device. The results generally show increased Beta activity, and a decreased ratio of theta activity to beta activity. Each of these is generally indicative of an increase in concentration.

Reading Task - Device On
Predominance of the cerebral rhythms by channel

|  | Theta | Beta 1 | Beta 2 | Beta 3 | Theta/(sum of Beta) | Results* |
|---|---|---|---|---|---|---|
| FP1 | 20.17% | 16.66% | 8.74% | 6.25% | 63.73% | Decreased Theta/Beta |
| FP2 | 18.77% | 14.86% | 7.93% | 6.37% | 64.37% | Decreased Theta/Beta |
| F7 | 18.49% | 16.87% | 10.98% | 7.23% | 52.71% | Decreased Theta/Beta |
| F3 | 13.73% | 20.73% | 11.94% | 7.44% | 34.23% | Decreased Theta/Beta |
| F8 | 18.26% | 20.25% | 11.39% | 9.53% | 44.35% | Decreased Theta/Beta |
| F4 | 21.50% | 21.53% | 14.42% | 8.43% | 48.45% | Decreased Theta/Beta |
| FZ | 21.18% | 15.79% | 10.30% | 7.57% | 62.92% | Decreased Theta/Beta |

FP1 & FP2 (Prefrontal Cortex) are key channels indicating concentration
*Desired result is Decreased Theta/Beta indicating higher concentration The data above, indicate that the test subject appears to have a higher level of concentration while wearing the device.

Relaxation

The same test subject was used to test the device's effect on relaxation. Here, the electrodes on the Occipital cortex (O1 and O2) are key channels for indicating relaxation.

Figure 16:
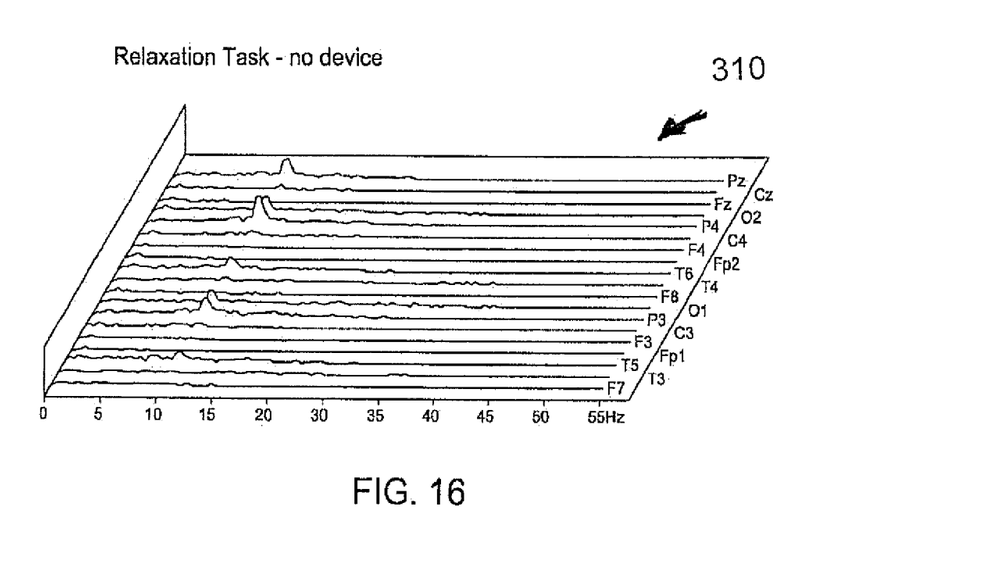

The table below and associated EEG readout 310 (FIG. 16) show the expected alpha predominance while relaxing.

Relaxation Task - No Device
Predominance of the cerebral rhythms by channel

|  | Alpha | Beta 1 | Beta 2 | Beta 3 | Sum Of Beta |
|---|---|---|---|---|---|
| O1 | 27.13% | 19.55% | 15.23% | 10.21% | 44.99% |
| O2 | 30.27% | 20.89% | 10.06% | 8.22% | 39.17% |
| T3 | 20.04% | 24.66% | 12.57% | 10.69% | 47.92% |
| T5 | 28.85% | 22.17% | 9.81% | 5.84% | 37.82% |
| P3 | 34.22% | 21.20% | 9.32% | 5.12% | 35.64% |
| F8 | 20.17% | 18.25% | 9.81% | 6.95% | 35.01% |
| T4 | 21.23% | 23.02% | 12.27% | 11.04% | 46.33% |
| T6 | 30.51% | 21.69% | 8.47% | 5.53% | 35.69% |
| F4 | 18.94% | 19.69% | 9.73% | 6.52% | 35.94% |
| P4 | 37.82% | 21.26% | 7.90% | 5.01% | 34.17% |
| PZ | 34.55% | 20.69% | 8.08% | 4.62% | 33.39% |

O1 & O2 (Occipital cortex) are key channels for indicating relaxation Control

Figure 17:
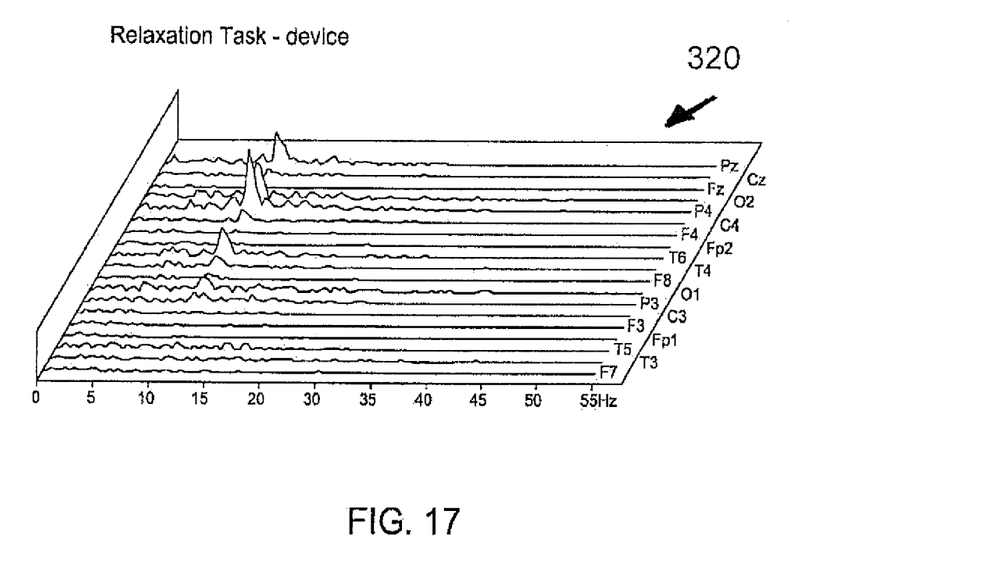

The table below, and associated EEG readout 320 (FIG. 17) show generally increased alpha activity, and decreased overall Beta activity when compared to the control, both indicative of enhanced relaxation.

Relaxation Task - Device On
Predominance of the cerebral rhythms by channel

|    | Alpha  | Beta 1 | Beta 2 | Beta 3 | Sum of Beta | Resulting Alpha* | Resulting total Beta* |
|----|--------|--------|--------|--------|-------------|------------------|-----------------------|
| O1 | 30.63% | 21.76% | 12.51% | 7.56%  | 41.83%      | Increased Alpha  | Decreased Beta sum    |
| O2 | 40.66% | 19.70% | 9.15%  | 7.65%  | 36.50%      | Increased Alpha  | Decreased Beta sum    |
| T3 | 20.82% | 23.49% | 13.13% | 11.66% | 48.28%      | Increased Alpha  | Increased Beta sum    |
| T5 | 22.22% | 25.83% | 12.49% | 6.69%  | 45.01%      | Decreased Alpha  | Increased Beta sum    |
| P3 | 27.82% | 25.48% | 11.57% | 6.73%  | 43.78%      | Decreased Alpha  | Increased Beta sum    |
| F8 | 27.85% | 13.39% | 11.06% | 9.72%  | 34.17%      | Increased Alpha  | Decreased Beta sum    |
| T4 | 34.57% | 18.78% | 8.56%  | 7.64%  | 34.98%      | Increased Alpha  | Decreased Beta sum    |
| T6 | 44.12% | 18.24% | 7.10%  | 5.89%  | 31.23%      | Increased Alpha  | Decreased Beta sum    |
| F4 | 21.03% | 17.44% | 12.73% | 8.64%  | 38.81%      | Increased Alpha  | Increased Beta sum    |
| P4 | 50.06% | 20.05% | 8.00%  | 4.57%  | 32.62%      | Increased Alpha  | Decreased Beta sum    |
| PZ | 42.22% | 19.64% | 9.08%  | 4.93%  | 33.65%      | Increased Alpha  | Increased Beta sum    |

O1 & O2 (Occipital Cortex) are key channels for indicating relaxation
*Desired result is Increased Alpha and Decreased Beta indicating a more relaxed state Thus, the data show that the device can be used to increase concentration if needed, as well as enhance relaxation when needed. Depending upon a patient's condition, either may be useful in the treatment or management of their condition or disorder.

For example, in patients with attention deficit disorder, those with the hyperactivity component may benefit from the enhance relaxation effect that can be triggered by the device. Those without the hyperactivity component can benefit from increased concentration. Either way, the device and methods of using it are flexible enough to allow for treatment of both conditions, when necessary.

The disclosure herein is meant to be illustrative in nature. Those of skill in the art will recognize additional variants of the invention which are within the scope and spirit of the invention disclosed here.

What is claimed is:

1. A method for treating a neurological disorder, the method comprising:
mechanically stimulating a vestibulocochlear nerve of a patient, wherein the stimulation comprises a first mechanical vibratory stimulus for mechanically stimulating the auditory nerve bundle of the vestibulocochlear nerve and second mechanical vibratory stimulus for mechanically stimulating the vestibular nerve bundle of the vestibulocochlear nerve, wherein the mechanical vibratory stimuli vibrate at different frequencies and are applied by a vibrating mechanism in contact with the patient.

2. The method of claim 1, wherein the mechanical vibratory stimuli are applied to both vestibulocochlear nerves of the patient.

3. The method of claim 1, wherein at least one of the mechanical vibratory stimuli is applied at a frequency of about 0.1 Hz to about 40 Hz.

4. The method of claim 3, wherein the other mechanical vibratory-stimulus is applied at a frequency of about 0.3 Hz to about 15 Hz.

5. The method of claim 1, wherein at least one of the mechanical vibratory stimuli is applied at a frequency of about 0.3 Hz to about 15 Hz.

6. The method of claim 1, wherein the first mechanical vibratory stimulus is applied to the auditory nerve bundle of the vestibulocochlear nerve, without affecting the vestibular nerve bundle.

7. The method of claim 1, wherein the second mechanical vibratory stimulus is applied to the vestibular nerve bundle, without affecting the auditory nerve bundle.

8. The method of claim 1, wherein the mechanical vibratory stimuli are applied externally and travel to the vestibulocochlear nerve via transmission through body tissues.

9. The method of claim 1, wherein the mechanical vibratory stimuli are applied within the patient's body and transmitted either directly to the auditory nerve bundle and the vestibular nerve bundle of the vestibulocochlear nerve or via transmission through body tissues.

10. A method of increasing concentration, the method comprising:
mechanically stimulating a vestibulocochlear nerve of a patient, wherein the stimulation comprises a first mechanical vibratory stimulus for mechanically stimulating the auditory nerve bundle of the vestibulocochlear nerve and a second mechanical vibratory stimulus for mechanically stimulating the vestibular nerve bundle of the vestibulocochlear nerve, wherein the mechanical vibratory stimuli are applied by a vibrating mechanism in contact with the patient to increase Beta brain wave activity.

11. A method of enhancing relaxation, the method comprising:
stimulating a vestibulocochlear nerve of a patient, wherein the stimulation comprises a first mechanical vibratory stimulus for stimulating the auditory nerve bundle of the vestibulocochlear nerve and second mechanical vibratory stimulus for stimulating the vestibular nerve bundle of the vestibulocochlear nerve, wherein the mechanical vibratory stimuli are applied by a vibrating mechanism in contact with the patient to increase alpha brain wave activity.

12. An apparatus for delivering a mechanical stimulus to the vestibulocochlear nerve of a patient, the apparatus comprising:
at least one mechanical vibratory element capable of delivering a complex mechanical vibration comprising a first mechanical vibratory stimulus between 0.1 Hz and about 40 Hz and a second mechanical vibratory stimulus between about 0.3 Hz and about 15 Hz; a microprocessor, operatively coupled to the vibratory element for controlling the delivery of stimuli via the at least one mechanical vibratory element, wherein the mechanical vibratory element is in contact with the patient.

13. The apparatus of claim 12, further comprising a second mechanical vibratory element capable of delivering a complex vibration comprising a first mechanical vibratory stimulus between 0.1 Hz and about 40 Hz and a second mechanical vibratory stimulus between about 0.3 Hz and about 15 Hz, wherein the second mechanical vibratory element is in contact with the patient and wherein the at least one mechanical vibratory element and the second mechanical vibratory element are independently controllable by the microprocessor.

14. The apparatus of claim 12, further comprising user controls for selective control of the stimuli.

15. The apparatus of claim 12, wherein the at least one mechanical vibratory element is adapted for placement externally behind the ear of a patient.

16. The apparatus of claim 12, wherein the at least one mechanical vibratory element is adapted for placement within the ear canal of a patient.

17. The apparatus of claim 12, wherein the at least one mechanical vibratory element is adapted for implantation at or near the vestibulocochlear nerve.

\* \* \* \* \*